United States Patent [19]

Zondler

[11] 3,957,820

[45] May 18, 1976

[54] PYRROLIDINES CONTAINING TWO PRIMARY AMINO GROUPS AND PROCESS FOR THEIR MANUFACTURE

[75] Inventor: Helmut Zondler, Allschwil, Switzerland

[73] Assignee: Ciba-Geigy Corporation, Ardsley, N.Y.

[22] Filed: July 17, 1974

[21] Appl. No.: 489,316

[30] Foreign Application Priority Data
July 25, 1973 Switzerland.................. 10839/73

[52] U.S. Cl. .................................. 260/326.85
[51] Int. Cl.$^2$................................. C07D 207/14
[58] Field of Search ........................ 260/326.85

[56] References Cited
UNITED STATES PATENTS
3,133,082   5/1964   Wu et al. ................ 260/326.85

Primary Examiner—Sam Rosen
Attorney, Agent, or Firm—Luther A. R. Hall

[57] ABSTRACT

The invention relates to 3-amino-4-aminomethyl-pyrrolidines which contain, in the 1-position of the heterocyclic ring, organic radicals as substituents, and in which also the H-atom in the 2-position of the heterocyclic ring can be substituted by an organic radical. The invention also relates to the preparation of these pyrrolidines by catalytic hydrogenation of the corresponding 3-amino-4-cyano-3-pyrrolines. Hydrogenation is preferably performed in the presence of $NH_3$. The amines according to the invention are suitable as curing agents for epoxide resins, as reactants for isocyanates, and as starting substances for polyamides.

13 Claims, No Drawings

PYRROLIDINES CONTAINING TWO PRIMARY AMINO GROUPS AND PROCESS FOR THEIR MANUFACTURE

The invention relates to 3-amino-4-aminomethylpyrrolidines and a process for their manufature. The preparation of 4-amino-3-aminomethylpiperdines by hydrogenation of 4-amino-3-cyano-1,2,5,6-tetrahydropyridines has already been described in the U.S. Pat. Nos. 3,717,593 and 3,718,610. A process for the preparation of 3-amino-4-aminomethyl-pyrrolidines, wherein, correspondingly, 3-amino-4-cyano-3-pyrrolines are hydrogenated, has not been hitherto known. By virtue of the changed steric conditions in the case of such N-heterocyclic 5-ring-cyano compounds (ring tension and screening effect), compared with those in the case of the pyridine derivatives, the possibility of a successful catalytic hydrogenation was scarcely to be anticipated.

This prejudice among experts was further strengthened by a publication of J. F. Cavalla in J.Chem.Soc. (1962) 4664-4672. One of the things referred to in this publication was the fact that a catalytic hydrogenation of the double bond in 3-amino-4-cyano-pyrrolines was not successful.

Notwithstanding the prejudice of the experts, it has been possible to achieve, in a surprising manner, the aim of this invention.

The invention relates to 3-amino-4-aminomethyl-pyrrolidines of formula I

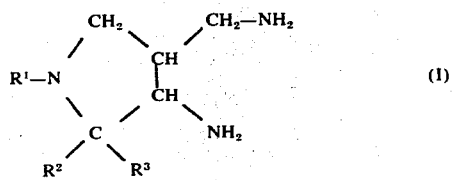

wherein
- R¹ represents a branched-chain or straight-chain alkyl radical having 1 to 12 carbon atoms, a cycloaliphatic radical having 6 carbon atoms, a benzyl radical, a substituted or unsubstituted phenyl radical or aminopropyl,
- R² represents hydrogen, a straight-chain or branched-chain alkyl radical having 1 to 12 carbon atoms, or an unsubstituted or substituted phenyl radical, and
- R₃ stands for hydrogen, or an alkyl radical having 1 to 6 carbon atoms, and
- R₂ and R₃ together can also represent a pentamethylene radical.

The 3-amino-4-aminomethyl-pyrrolidines of formula I are obtained by hydrogenation of 3-amino-4-cyano-3-pyrrroline of formula II

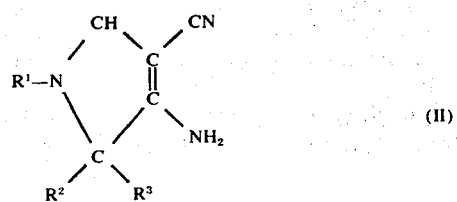

at a temperature of about 20° to 150°C, preferably in the presence of ammonia and under excess pressure, and the resulting product is separated, in a known manner, from catalyst and solvent, and optionally distilled.

The appropriate temperature for the hydrogenation process according to the invention is dependent in each case on the hydrogenation catalyst used. Where Raney nickel or Raney cobalt is employed, the optimum operating conditions, with regard to yield, are obtained with the use of temperatures of about 60° to 120°C. With the application of known noble metal catalysts, such as platinum, palladium, rhodium or ruthenium, it is also possible to work at lower temperatures, such as at about room temperature.

The hydrogenation reaction is performed by methods common in the laboratory and in industry; it is preferably carried out under pressure in an autoclave. A preferred embodiment of the invention is where hydrogenation is performed in the presence of ammonia. It is essential in this case that the operation is performed under pressure, in order to prevent the escape of ammonia. A small excess pressure even of, for example, 1 atmosphere will generally suffice. Usually, however, the reaction according to the invention is performed at between 50 and 300 atmospheres.

As solvents for the hydrogenation reaction, it is possible to use the organic solvents that are usually applied together with the above mentioned catalyst types, particularly alcohols, hydrocarbons or ethers, such as methanol, ethanol and dioxane, and also aromatic hydrocarbons, such as toluene or benzene. A preferred embodiment of the process according to the invention incorporates the use of ammonia as solvent.

The catalytic reduction is as a rule carried out by mixing the solution of the respective 3-amino-4-cyano-3-pyrroline with the catalyst, and then introducing into the reaction mixture firstly ammonia and afterwards hydrogen gas. Hydrogenation is continued until no further hydrogen is absorbed. After completion of hydrogenation, the catalyst is separated, e.g. by filtration, and the solvent is distilled off in vacuo at a moderate temperature.

It suffices in some cases just to separate the final product from the catalyst and the solvent in the described manner. The resulting crude 3-amino-4-aminomethyl-pyrrolidine can then be directly further employed undistilled.

Frequently, however, higher requirements have to be met with respect to the degree of purity of the products obtained by the processes according to the invention, and in such cases distillation is performed. The necessary conditions for distillation can vary from product to product. With substances having a low molecular weight, a vacuum of a few mm of Hg is often adequate, and temperatures of only up to about 100°C are required. In some cases, however, a high vacuum is necessary for distillation.

A purification of the resulting crude products by washing out or extracting with suitable organic solvents would in principle also be feasible.

Starting substances used for the process according to the invention are preferably such 3-amino-4-cyano-3-pyrrolines of formula II wherein R¹ represents one of the radicals —CH₃, —C(CH₃)₃, —CH(CH₃)₂, —(CH₂)₉—CH₃, —CH₂—CH₂—CN,

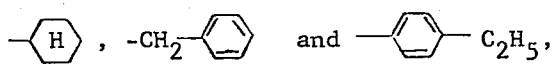

$R^2$ represents hydrogen or one of the radicals —$CH_3$, —$CH(CH_3)_2$, —$(CH_2)_8$—$CH_3$ and

, and $R^3$ represents hydrogen or one of the radicals —$CH_3$ and —$CH_2$—$CH_2$—$CH(CH_3)_2$. Substances also suitable are, in particular, those of formula II wherein $R^2$ and $R^3$ in formula II together represent an alkylene radical, such as, for example, pentamethylene.

Suitable starting substances of formula II for the process according to the invention are, for example, the following 3-amino-4-cyano-3-pyrrolines:

3-amino-4-cyano-1-isopropyl-3-pyrroline,
3-amino-4-cyano-1,2-dimethyl-3-pyrroline,
3-amino-4-cyano-1-decyl-2-methyl-3-pyrroline,
3-amino-4-cyano-1-cyclohexyl-2-methyl-3-pyrroline,
3-amino-4-cyano-1-benzyl-2-methyl-3-pyrroline,
3-amino-4-cyano-1-tert.butyl-2-methyl-3-pyrroline, and
1-methyl-4-amino-3-cyano-1-aza-spiro[4,5]-decene-3.

The preparation of the starting products according to formula II is carried out according to Cavalla. It has been described in the above-mentioned publication. According to this method, cyanohydrines, which are prepared from aldehydes or ketones, are condensed with monocyanoethylated, aromatic or aliphatic amines, with the splitting-off of water, to the corresponding dinitrile. The dinitriles are further reacted, in the presence of basic catalysts (e.g. Na-tert.butylate) and in the presence of tert.butanol, to 3-amino-4-cyano-3-pyrroline (Thorpe-Ziegler-cyclisation). There are obtained by this method the substances listed in the following table in good yields (up to 85% of theory).

The stated compounds are all suitable as starting products for preparation of the pyrrolidines of formula I.

TABLE

3-Amino-4-cyano-3-pyrrolines of formula II prepared according to the method of Cavalla.

| $R_1$ | $R_2$ | $R_3$ | M.P. °C |
|---|---|---|---|
| $CH_3$— | $CH_3$— | H— | 149–152 |
| $(CH_3)_2CH$— | $CH_3$— | H— | 110–111 |
| $(CH_3)_3C$— | $CH_3$— | H— | 145–146 |
| $CH_3(CH_2)_3$— | $CH_3$— | H— | 105 |
| $CH_3(CH_2)_5$— | $CH_3$— | H— | 96–97 |
| $CH_3(CH_2)_9$— | $CH_3$— | H— | 91–92 |
| cyclohexyl | $CH_3$— | H— | 128–129 |
| benzyl ($C_6H_5CH_2$—) | $CH_3$— | H— | 108 |
| $H_5C_2$—$C_6H_4$— | $CH_3$— | H— | 160–162 |
| $NCCH_2CH_2$— | $CH_3$— | H— | 118–121 |
| $(CH_3)_2CH$— | H— | H— | 133–134 |
| $(CH_3)_2CH$— | $(CH_3)_2CH$— | H— | 88–88,5 |
| $(CH_3)_3C$— | $(CH_3)_2CH$— | H— | 104–107 |
| $CH_3$— | phenyl | H— | 178–180 |
| $CH_3O$—$C_6H_4$— | phenyl | H— | 192–194 |
| $CH_3$— | —$(CH_2)_8CH_3$ | H— | 79,5–81,5 |
| $CH_3$— | $CH_3$— | $CH_3$— | 149–150 |
| $CH_3$— | $CH_3$— | —$CH_2CH_2CH(CH_3)_2$ | 83,5–85 |
| $CH_3$— | $R_2 + R_3 =$ —$(CH_2)_5$— | | 120–122 |

3-amino-4-cyano-1-(p-ethylphenyl)-2-methyl-3-pyrroline,
3-amino-4-cyano-1,2-diisopropyl-3-pyrroline,
3-amino-4-cyano-1-methyl-2-nonyl-3-pyrroline,
3-amino-4-cyano-1-methyl-2-phenyl-3-pyrroline,
3-amino-4-cyano-1-(β-cyanoethyl)-2-methyl-3-pyrroline,
3-amino-4-cyano-1,2,2-trimethyl-3-pyrroline,
3-amino-4-cyano-1,2-dimethyl-2-isopentyl-3-pyrroline, The 3-amino-4-aminomethyl-pyrrolidines of formula I prepared by the process according to the invention are valuable curing agents for epoxide resins. As diamines, they are also suitable for the preparation of polyamides, or as reaction components for isocyanates (polyurea manufacture). Furthermore, they would be of particular value also as organic intermediate products.

Therefore, they constitute an outstanding contribution to the stock of technical knowledge.

The invention is further illustrated by the following examples.

EXAMPLE 1

3-Amino-4-aminomethyl-1-isopropyl-pyrrolidine 134 g of 3-amino-4-cyano-1-isopropyl-3-pyrroline is placed together with 200 ml of ethanol and 10.5 g of Raney nickel, containing 2% of palladium, into an autoclave, into which is then introduced under pressure 200 g of gaseous ammonia. Hydrogen is subsequently injected at room temperature to a pressure of 100 atm., and hydrogenation is performed at 120°C. Already after 1 hour, after a decrease in pressure, there is established a constant pressure, and hydrogenation is complete. The catalyst is filtered off under suction, and the reaction mixture is concentrated in a rotary evaporator at a bath temperature of 45°C and a pressure of 15 mm Hg to obtain 140.5 g of residue containing, on the basis of the gas-chromatogram, besides an amount of ethanol, only slight amounts (<10%) of by-products. Distillation through a packed column yields 91.8 g (66% of theory); the principal amount boils at 58°C/0.1 mm Hg.

Analysis: $C_8H_{19}N_3$ (M = 157.26). Calculated: C, 61.10; H, 12.18; N, 26.72. Found: C, 60.98; H, 12.35; N, 26.61.

EXAMPLE 2

3-Amino-4-aminomethyl-1,2-dimethyl-pyrrolidine a. Hydrogenation in the presence of ammonia By a procedure analogous to that described in Example 1, 100 g of 3-amino-4-cyano-1,2-dimethyl-3-pyrroline is placed with 300 ml of ethanol and 100 g of gaseous ammonia, together with 10 g of Raney nickel containing 2% of palladium, into an autoclave, and hydrogenation is performed for 3 hours at 120°C under a pressure of 100 atmospheres. The catalyst is filtered off with suction, and the solvent is removed at 50°C bath temperature at a pressure of 15 mm Hg to obtain 97 g of crude amine which contains, on the basis of the gas-chromatogram, besides an amount of ethanol, about 10–15% of low-boiling by-products. Distillation of the crude amine yields 75.0 g of distillable fractions, B.P. 95°–130°C/7 mm Hg, which are further purified through a spinning band column. There is obtained 59.0 g (56.5%), B.P. 98°–101°C/8 mm Hg.

Analysis $C_7H_{17}N_3$ (M = 143.23). Calculated: C, 58.70; H, 11.96; N, 29.34. Found: C, 58.18; H, 12.17; N, 28.97.

b. Hydrogenation without ammonia

By a procedure comparable with (a), 50 g of the same starting product in 400 ml of ethanol is hydrogenated, in the presence of 5 g of the same catalyst, at 120°C under 100 atmospheres. Processing analogous to that under (a) yields 50 g of crude amine containing, on the basis of the gas-chromatogram thereof, appreciable amounts of high- and low-boiling by-products. The desired main product is present in an amount of about 30–40%, relative to all fractions of the crude amine.

EXAMPLE 3

3-Amino-4-aminomethyl-1-decyl-2-methyl-pyrrolidine

In a manner analogous to that in Example 1, 110 g of 3-amino-4-cyano-1-decyl-2-methyl-3-pyrroline in 200 ml of ethanol and 200 g of gaseous ammonia is hydrogenated, in the presence of 6 g of Raney nickel containing 2% of palladium, at 120°C at a pressure of 100 atmospheres. By analogous processing, there is obtained 111 g of crude amine, in which the presence of about 10% of low-boiling by-products can be detected by gas-chromatography. Fractional distillation through a packed column yields an amount of 67.1 g (59.4%), B.P. 132°–134°C/0.14 mm Hg.

Analysis $C_{16}H_{35}N_3$ (M = 269.46). Calculated: C, 71.31; H, 13.09; N, 15.60. Found: C, 71.31; H, 13.31; N, 15.64.

EXAMPLE 4

3-Amino-4-aminomethyl-1-cyclohexyl-2-methyl-pyrrolidine

By a process analogous to that described in Example 1, 965 g of 3-amino-4-cyano-1-cyclohexyl-2-methyl-3-pyrroline in 1940 ml of ethanol and 1940 g of gaseous ammonia is hydrogenated, in the presence of 48 g of Raney nickel (without palladium), for 3 hours at 120°C at a pressure of 100 atmospheres. The catalyst is filtered off under suction, and concentration is performed at 60°C bath temperature at a pressure of 15 mm Hg to obtain 977 g of crude amine, in which can be detected, by gas-chromatography, about 10% of low-boiling by-products. Fraction distillation through a packed column yields 819 g (82.4%) of pure amine, B.P. 122°C/0.22 to 129°C/0.80 mm Hg.

Analysis $C_{12}H_{25}N_3$ (M = 211.34). Calculated: C, 68.19; H, 11.92; N, 19.88. Found: C, 68.14; H, 11.83; N, 19.74.

EXAMPLE 5

3-Amino-4-aminomethyl-1-benzyl-2-methyl-pyrrolidine

In a manner to that in Example 1, 106.6 g of 3-amino-4-cyano-1-benzyl-2-methyl-3-pyrroline in 200 ml of ethanol and 200 g of gaseous ammonia is hydrogenated, in the presence of 6 g of Raney nickel containing 2% of palladium, for 4 hours at 120°C at a pressure of 100 atmospheres. The crude amine contains, on the basis of the gas-chromatogram, about 10% of low-boiling by-product. Fractional distillation through a packed column yields 52.1 g (47.6%), B.P. 126°–127°C/0.3 mm Hg.

Analysis $C_{13}H_{21}N_3$ (M = 219.32). Calculated: C, 71.19; H, 9.65; N, 19.16. Found: C, 70.97; H, 9.59; N, 18.81.

EXAMPLE 6

3-Amino-4-aminomethyl-1-(p-ethyl-phenyl)-2-methyl-pyrrolidine

By a procedure analogous to that described in Example 1, 116.5 g of 3-amino-4-cyano-1-(p-ethyl-phenyl)-2-methyl-3-pyrroline in 250 ml of ethanol and 200 g of gaseous ammonia is hydrogenated, in the presence of 11 g of Raney nickel containing 2% of palladium, for 5 hours at 120°C at a pressure of 100 atmospheres. Processing analogous to that in Example 1 yields 120.2 g of crude amine containing, according to the gas-chromatogram thereof, less than 10% of low-boiling by-products. Fractional distillation through a packed column is performed to obtain 94.8 g (79.3%) of pure amine, B.P. 135°C/0.011 mm Hg to 147°C/0.022 mm Hg.

Analysis $C_{14}H_{23}N_3$ (M = 233.35). Calculated: C, 72.05; H, 9.94; N, 18.01. Found: C, 71.78; H, 9.92; N, 17.78.

EXAMPLE 7

3-Amino-4-aminomethyl-1,2-diisopropyl-pyrrolidine

In a manner analogous to that in Example 1, 115.4 g of 3-amino-4-cyano-1,2-diisopropyl-3-pyrroline in 250 ml of ethanol and 200 g of gaseous ammonia are hydrogenated, in the presence of 11.5 g of Raney nickel containing 2% of palladium, for 4 hours at 120°C at a pressure of 100 atmospheres. The catalyst is filtered off under suction, and the solvent is removed to obtain 119 g of crude amine which contains, according to the gas-chromatogram, about 10% of low-boiling fractions, besides ethanol. Fractional distillation through a packed column yields 57.5 g (48.5%) of pure amine, B.P. 64°C/0.012 mm Hg.

Analysis $C_{11}H_{25}N_3$ (M = 199.33). Calculated: C, 66.04; H, 12.49; N, 21.29. Found: C, 66.28; H, 12.64; N, 21.08.

EXAMPLE 8

3-Amino-4-aminomethyl-1-methyl-2-nonyl-pyrrolidine

In a manner analogous to that described in Example 1, 203 g of 3-amino-4-cyano-1-methyl-2-nonyl-3-pyrroline in 600 ml of ethanol and 300 g of gaseous ammonia are hydrogenated, in the presence of 20 g of Raney nickel containing 2% of palladium, for 3 hours at 120°C at a pressure of 100 atmospheres. Distillative processing through a packed column yields 147.5 g (72.0%) of pure amine, B.P. 135°–137°C/0.26 mm Hg.

Analysis $C_{15}H_{33}N_3$ (M = 255.44). Calculated: C, 70.53; H, 13.02; N, 16.45. Found: C, 70.63; H, 13.27; N, 16.62.

EXAMPLE 9

3-Amino-4-aminomethyl-1-methyl-2-phenyl-pyrrolidine

By a procedure analogous to that given in Example 1, 140 g of 3-amino-4-cyano-1-methyl-2-phenyl-3-pyrroline in 420 ml of ethanol and 140 g of gaseous ammonia are hydrogenated, in the presence of 8 g of Raney nickel containing 2% of palladium, for 6 hours at 120°C at a pressure of 100 atmospheres. Processing as in Example 1 yields 140.2 g of crude amine which, according to the gas-chromatogram, is about 75% pure. There is obtained, by distillative preparation through a packed column, 65 g of pure amine (46%), B.P. 115°C/0.25 mm Hg to 119°C/0.28 mm Hg.

Analysis $C_{12}H_{19}N_3$ (M = 205.30). Calculated: C, 70.20; H, 9.33; N, 20.47. Found: C, 70.05; H, 9.52; N, 20.49.

EXAMPLE 10

3-Amino-4-aminomethyl-1-aminopropyl-2-methyl-pyrrolidine

In a manner analogous to that described in Example 1, 106 g of 3-amino-4-cyano-1-(β-cyanoethyl)-2-methyl-3-pyrroline in 200 ml of ethanol and 200 g of gaseous ammonia are hydrogenated, in the presence of 7 g of Raney nickel containing 2% of palladium, for 7 hours at 120°C at a pressure of 100 atmospheres. Processing as in Example 1 gives 108.5 g of crude amine, and distillation of this through a packed column yields 56 g (50.2%) of pure amine, B.P. 102°C/0.15 mm Hg to 118°C/0.45 mm Hg.

Analysis $C_9H_{22}N_4$ (M = 186.30). Calculated: C, 58.02; H, 11.90; N, 30.08. Found: C, 57.89; H, 12.05; N, 29.91.

EXAMPLE 11

3-Amino-4-aminomethyl-1,2,2-trimethyl-pyrrolidine

By a procedure analogous to that in Example 1, 1166 g of 3-amino-4-cyano-1,2,2-trimethyl-3-pyrroline in 2300 ml of ethanol and 1860 g of gaseous ammonia are hydrogenated, in the presence of 85 g of Raney nickel, at 120°C in an autoclave at a pressure of 100 atmospheres to constant pressure. Distillative processing of the mixture gives 776 g of pure amine (64%) which boils at between 101° and 104°C/7 mm Hg.

Analysis $C_8H_{19}N_3$ (M = 157.26). Calculated: C, 61.10; H, 12.18; N, 26.72. Found: C, 61.39; H, 12.36; N, 26.95.

EXAMPLE 12

3-Amino-4-aminomethyl-1,2-dimethyl-2-isopentyl-pyrrolidine

By a procedure analogous to that in Example 1, 99 g of 3-amino-4-cyano-1,2-dimethyl-2-isopentyl-3-pyrroline in a mixture of 200 ml of ethanol and 160 g of gaseous ammonia is hydrogenated, in the presence of 10 g of Raney nickel, at 120°C in an autoclave at an initial pressure of 100 atmospheres. Purification of the amine through a spinning band column yields 29.0 g of pure amine, B.P. 141°–142°C/7 mm Hg.

Analysis $C_{12}H_{27}N_3$ (M = 213.36). Calculated: C, 67.55; H, 12.76; N, 19.70. Found: C, 67.42; H, 12.47; N, 19.57.

EXAMPLE 13

3-Amino-4-aminomethyl-1-tert.butyl-2-methyl-pyrrolidine

In a manner analogous to that described in Example 1, 308 g of 3-amino-4-cyano-1-tert.butyl-2-methyl-3-pyrroline in a mixture of 620 ml of ethanol and 620 g of gaseous ammonia is hydrogenated, in the presence of 30 g of Raney nickel, for 3 hours at 120°C at a pressure of 100 atmospheres. Distillative processing of the mixture yields 270.5 g (85.0% of theory) of pure amine, B.P. 68°–71°C/0.20 mm Hg.

Analysis $C_{10}H_{23}N_3$ (M = 185.31). Calculated: C, 64.81; H, 12.51; N, 22.68. Found: C, 64.65; H, 12.47; N, 22.38.

EXAMPLE 14

1-Methyl-4-amino-3-aminomethyl-1-aza-spiro[4,5]-decane

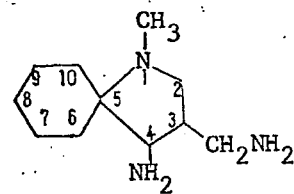

In a manner analogous to that in Example 1, 1633 g of 1-methyl-4-amino-3-cyano-1-aza-spiro[4,5]-decane in 3.0 l of ethanol and 3.0 kg of gaseous ammonia is hydrogenated, in the presence of 90 g of Raney nickel, in three autoclave charges, at 120°–125°C at an initial pressure of 100 atmospheres to constant pressure. Distillative processing of the hydrogenated product by means of a packed column yields 1333.5 g (81.6% of theory) of pure amine, B.P. 91°C/0.17 mm Hg to 98°C/0.20 mm Hg. The principal amount distills at 96°C/0.17 mm Hg.

Analysis $C_{11}H_{23}N_3$ (M = 197.32). Calculated: C, 66.95; H, 11.75; N, 21.30. Found: C, 66.79; H, 11.86; N, 20.94.

What we claim is:

1. A —3-amino-4-aminomethyl)-pyrrolidine of formula I

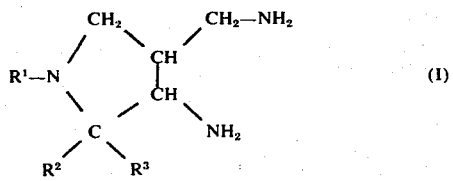

wherein
$R^1$ represents a branched-chain or straight-chain alkyl radical having 1 to 12 carbon atoms, a cycloaliphatic radical having 6 carbon atoms, a benzyl radical, a phenyl, p-ethyl-phenyl or p-methoxyphenyl radical or aminopropyl,
$R^2$ represents hydrogen, a straight-chain or branched-chain alkyl radical having 1 to 12 carbon atoms, or a phenyl radical, and
$R^3$ stands for hydrogen, or for an alkyl radical having 1 to 6 carbon atoms, or
$R^2$ and $R^3$ together represent a pentamethylene radical.

2. A 3-amino-4-aminomethyl-pyrrolidine according to claim 1, wherein $R^1$ in formula I represents one of the radicals —$CH_3$, —$C(CH_3)_3$, —$CH(CH_3)_2$, —$(CH_2)_9$—$CH_3$, —$CH_2$—$CH_2$—$CH_2$—$NH_2$,

3. A 3-amino-4-aminomethyl-pyrrolidine according to claim 1, wherein $R^2$ in formula I represents one of the radicals —$CH_3$, —$CH(CH_3)_2$, —$(CH_2)_8$—$CH_3$ and

4. A 3-amino-4-aminomethyl-pyrrolidine according to claim 1, wherein $R^2$ and $R^3$ together represent the radical —$(CH_2)_5$—.

5. A 3-amino-4-aminomethyl-pyrrolidine according to claim 1, wherein $R^3$ represents hydrogen or one of the radicals —$CH_3$ and —$CH_2$—$CH_2$—$CH(CH_3)_2$.

6. A diamine as claimed in claim 1 which is 3-amino-4-aminomethyl-1-cyclohexyl-2-methyl-pyrrolidine.

7. A diamine as claimed in claim 1 which is 3-amino-4-aminomethyl-1-methyl-2-phenyl-pyrrolidine.

8. A diamine as claimed in claim 1 which is 3-amino-4-aminomethyl-1-aminopropyl-2-methyl-pyrrolidine.

9. A diamine as claimed in claim 1 which is 3-amino-4-aminomethyl-1,2,2-trimethyl-pyrrolidine.

10. A diamine as claimed in claim 1 which is 1-methyl-4-amino-3-aminomethyl-1-aza-spiro[4,5]-decane.

11. A process for the manufacture of a 3-amino-4-aminomethyl-pyrrolidine of formula I according to claim 1 characterized that a 3-amino-4-cyano-3-pyrroline of formula II

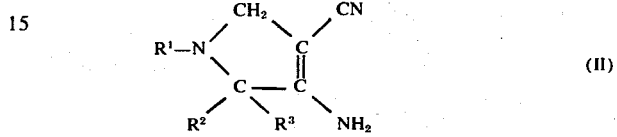

wherein
$R^1$ represents a branched-chain or straight-chain alkyl radical having 1 to 12 carbon atoms, a cycloaliphatic radical having 6 carbon atoms, a benzyl radical, a phenyl, p-ethylphenyl or p-methoxyphenyl radical or aminopropyl,
$R^2$ represents hydrogen, a straight-chain or branched-chain alkyl radical having 1 to 12 carbon atoms, or a phenyl radical, and
$R^3$ stands for hydrogen, or an alkyl radical having 1 to 6 carbon atoms, and
$R^2$ and $R^3$ together can also represent a pentamethylene radical, is hydrogenated at a temperature of between about 20° and 150°C in the presence of a hydrogenation catalyst and of ammonia and under a superimposed hydrogen pressure of 1 to 300 atmospheres.

12. A process according to claim 11, wherein hydrogenation is performed at a temperature of between 60° and 140°C and wherein no further solvent is used in addition to ammonia.

13. A process according to claim 11, wherein there are used compounds of formula II wherein $R^1$ represents one of the radicals —$CH_3$, —$C(CH_3)_3$, —$CH(CH_3)_2$, —$(CH_2)_9$—$CH_3$, —$CH_2$—$CH_2$—$CN$,

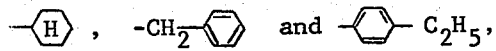

$R^2$ represents hydrogen or one of the radicals —$CH_3$, —$CH(CH_3)_2$, —$(CH_2)_8$—$CH_3$ and

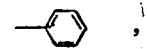

or wherein $R^2$ and $R^3$ together represent the radical —$(CH_2)_5$— and wherein $R^3$ represents hydrogen or one of the radicals —$CH_3$ and —$CH_2$—$CH_2$—$CH(CH_3)_2$.

* * * * *